United States Patent [19]

Fehr et al.

[11] Patent Number: 4,900,870
[45] Date of Patent: Feb. 13, 1990

[54] PROCESS FOR THE PREPARATION OF CYCLOALIPHATIC KETONES

[75] Inventors: Charles Fehr, Versoix; José Galindo, Geneva, both of Switzerland

[73] Assignee: Firmenich S.A., Geneva, Switzerland

[21] Appl. No.: 91,640

[22] Filed: Sep. 1, 1987

[30] Foreign Application Priority Data

Sep. 19, 1986 [CH] Switzerland ............ 3760/86-9

[51] Int. Cl.[4] ............................................. C07C 45/42
[52] U.S. Cl. .................................. 568/354; 568/356
[58] Field of Search ............................. 568/354, 356

[56] References Cited

U.S. PATENT DOCUMENTS 3,887,625 6/1975 Schulte-Ell .................... 568/376

FOREIGN PATENT DOCUMENTS 1449339 9/1976 United Kingdom ............ 549/320

OTHER PUBLICATIONS

Naef et al., Tetrahedron, vol. 42, pp. 3245–3250 (1980).
Watanabe et al., Aust. J. Chem, vol. 35, pp. 1739–1741 (1982).
Kitsukawa, Chem. Abst, vol. 80, #107366c (1974).
Watanabe et al., Chem. Abst, vol. 92, #110486v (1980).
Kikkawa et al., Chem. Abst, vol. 94, #139671d (1981).
Watanabe et al., Chem. Abst, vol. 87, #133828u (1977).

*Primary Examiner*—James H. Reamer
*Attorney, Agent, or Firm*—Pennie & Edmonds

[57] ABSTRACT

Process for the preparation of cycloaliphatic ketones of formula

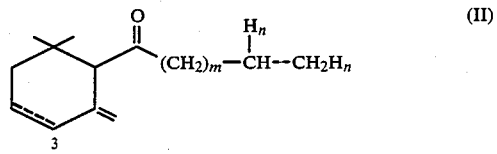

wherein index m designates integer 0, 1 or 2, n stands for 0 or 1 and the dotted lines represent an optional supplemental bond, which process consists in the deprotonation of an ester of formula

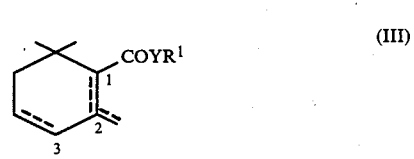

having either an isolated double bond in position 1 or 2 (exocyclic), or two conjugated double bonds in position 1 and 3 or 2 (exocyclic) and 3 as indicated by the dotted lines, and wherein symbol R' represents a linear or branched alkyl radical, preferably a $C_1$–$C_6$ alkyl radical, or a substituted or unsubstituted phenyl, and Y designates an oxygen or a sulphur atom, the deprotonation being followed by the addition of an organo-metallic compound of formula

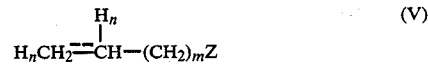

wherein m and n have the meaning defined above and Z represents a MgX radical or an alkali metal, preferably lithium, X defining a halogen and the dotted lines an optional supplemental bond, and finally a hydrolysis.

8 Claims, No Drawings

PROCESS FOR THE PREPARATION OF CYCLOALIPHATIC KETONES

BRIEF SUMMARY OF THE INVENTION

The instant invention relates to the field of organic synthesis and more particularly, it relates to a process for the preparation of cycloaliphatic ketones of formula

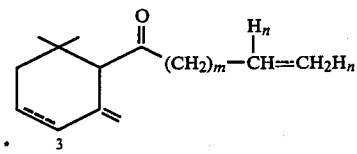
(II)

wherein index m designates integer 0, 1 or 2, n stands for 0 or 1 and the dotted lines represent an optional supplental bond, which comprises effecting the following subsequent reaction steps:

a. deprotonation of an ester of formula

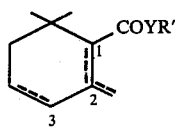
(III)

having either an isolated double bond in position 1 or 2(exocyclic), or two conjugated double bonds in position 1 and 3 or 2(exocyclic) and 3 as indicated by the dotted lines, and wherein symbol R' represents a linear or branched alkyl radical, preferably a $C_1$-$C_6$ alkyl radical, or a substituted or unsubstituted phenyl, and Y designates an oxygen or a sulphur atom;

b. addition to the thus formed enolate of formula

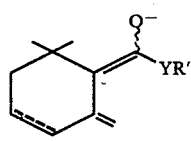
(IV)

of an organo-metallic compound of formula

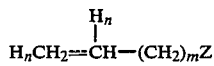
(V)

wherein m stands for integer 0, 1 or 2, n has the value of 0 or 1, Z represents a MgX radical or an alkali metal, preferably lithium, X designating a halogen atom, and the dotted lines represent an optional supplemental bond;

c. hydrolysis of the resulting product.

BACKGROUND OF THE INVENTION

Gamma-damascone, as well as gamma-damascenone, or 2-methylene-6,6,-dimethyl-1-crotonoyl-cyclohexane and 2-methylene-6,6-dimethyl-1-crotonoylcyclohex-3-ene respectively, and their alpha- and beta-isomers and their derivatives possessing a butanoyl side chain, represent very useful ingredients for the industry of perfumery and flavors alike.

These compounds obey to the generic formula

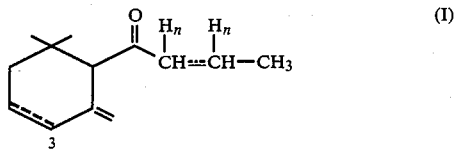
(I)

wherein the dotted lines represent an optional supplemental bond and wherein index n stands for 0 or 1 [see to this effect: U.S. Pat. Nos. 3,928,456, 3,975,310 and 4,226,892].

There is a constant need to dispose of more convenient and economical sources of these compounds and the present invention offers a novel solution to the problem represented by their synthesis.

THE INVENTION

Thanks to the invention process, it is now possible to obtain advantageously the precursors of formula

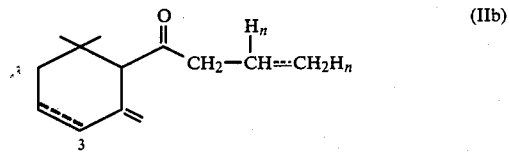
(IIb)

wherein index n and the dotted lines have the meaning indicated above, which compounds can subsequently be readily converted into their derivatives of formula (I) by means of an isomerization according to known methods, for instance by treatment with an acidic reagent.

One of the objects of the present invention consists in a process for the preparation of cycloaliphatic ketones of formula

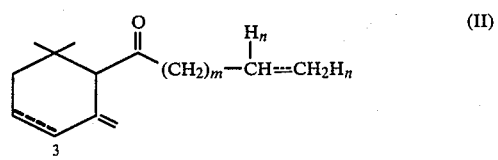
(II)

wherein index m designates integer 0, 1 or 2, n stands for 0 or 1 and the dotted lines represent an optional supplemental bond, which comprises effecting the following subsequent reaction steps:

a. deprotonation of an ester of formula

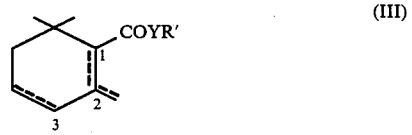
(III)

having either an isolated double bond in position 1 or 2(exocyclic), or two conjugated double bonds in position 1 and 3 or 2(exocyclic) and 3 as indicated by the dotted lines, and wherein symbol R' represents a linear or branched alkyl radical, preferably a $C_1$-$C_6$ alkyl radical, or a substituted or unsubstituted phenyl, and Y designates an oxygen or a sulphur atom;

b. addition to the thus formed enolate of formula

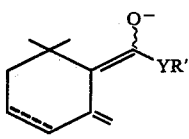
(IV)

of an organo-metallic compound of formula $$H_nCH_2=\overset{\overset{\displaystyle H_n}{|}}{C}H-(CH_2)_mZ \qquad (V)$$

wherein m stands for integer 0, 1 or 2, n has the value of 0, or 1, Z represents a MgX radical or an alkali metal, preferably lithium, X designating a halogen atom, and the dotted lines represent an optional supplemental bond;

c. hydrolysis of the resulting product.

The above described process is illustrated by the following reaction scheme:

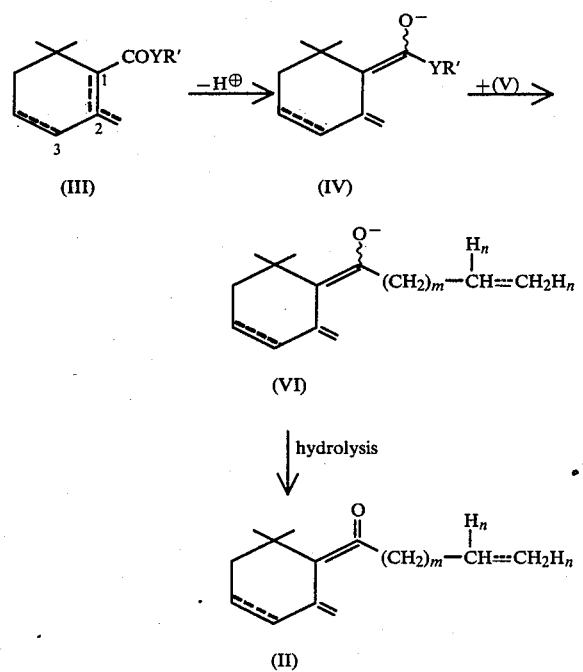

Suitable starting materials of formula (III) include cycloaliphatic esters chosen among the group of lower alkyl esters of beta- or gamma-cyclogeranic acid or of beta- or gamma-safranic acid. To this end, it would be convenient to mention methyl, ethyl, propyl, isopropyl and butyl beta- or gamma-cyclogeranate or beta- or gamma-safranate. All the above mentioned esters are commercially available or can be readily synthesized according to known methods. Preferred esters are methyl beta- or gamma-cyclogeranate and methyl or ethyl beta-safranate.

As starting materials for the invention process, it is also possible to utilize thioester derivatives. For instance, it would be possible to use S-phenyl beta-thiocyclogeranate.

The first step of the invention process, which consists in the deprotonation of the said starting esters, is carried out by means of a strong base. Suitable bases include alkyl derivatives of an alkali metal, such as for example propyl or butyl-lithium, or an alkali metal amide, preferably lithium amide. Thus, bases such as lithium dimethyl-, lithium diethyl- or lithium diisopropyl-amide represent preferred strong bases. Mixtures consisting of two of the cited bases can also be employed.

The reaction is carried out in inert organic solvents, for example by dissolving the starting ester in an ether such as tetrahydrofuran and the chosen base in an aliphatic, cycloaliphatic or aromatic hydrocarbon, for instance hexane, cyclohexane, benzene or toluene.

Without precluding the correctness of the mechanistic interpretation of the reaction which characterizes this first step of the process, we can assert that the product formed occurs in the form of a transient intermediate in the chosen reaction conditions. Indirect evidence tends to confirm however its structure. It has been possible in fact to isolate a silyl derivative of formula

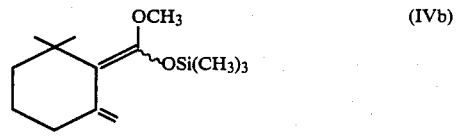
(IVb)

by adding trimethyl silyl chloride to the reaction mixture, after treating methyl gamma- or beta-cyclogeranate with a strong base according to the invention. This fact suggests that the transient intermediate is very probably present in the form of an enolate such as indicated by formula (IV), which compound could originate either from the direct deprotonation of ester (III), or from the action of the strong base utilized (or of a nucleophile) on the acetal ketene of formula (IVb) according to the following reaction scheme:

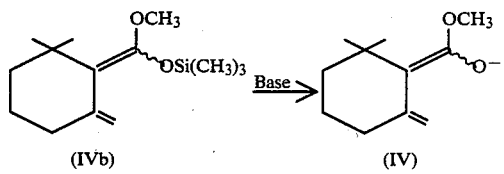

With regard to the reaction temperature of this first step of the invention process, this can be of about room temperature or slightly lower than room temperature, for example of about 15° to 25° C. According to a preferred embodiment, by using n-butyl-lithium as a base and methyl beta-cyclogeranate as starting ester, the reaction can be effected at about 15° C.

Lower temperatures can also be used. For example, by treating S-phenyl 2,6,6-trimethyl-1-cyclohex-1-en-1-carbothioate with butyl-lithium, the reaction can easily be carried out at −78° C.

Suitable organo-metallic compounds of formula (V) include alkyl or allyl halomagnesium derivatives such as allyl-magnesium chloride or bromide or methyl-, ethyl-, propyl- or butyl-lithium.

These compounds can be obtained according to well-known methods in the art starting from the chosen alkyl or allyl halides by reacting them with magnesium metal, usually in an ether solution under Grignard-type reaction conditions. As organo-metallic reactant, it is also possible to use an alkali metal alkyl compound, for example butyl-lithium. This enables the preparation of ketone compound (II) having a saturated side chain (n=1):

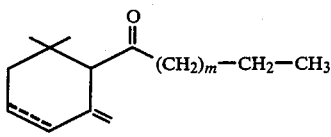

The last step of the invention process consists in the hydrolysis of the resulting product by treatment with water, preferably in a slightly acidic medium, for example by means of an icy ammonium chloride aqueous solution. The usual treatments of phase separation, neutralization and distillation enable to obtain the desired products.

The invention is illustrated in a more detailed manner by the following examples without being limited thereto. The temperatures are indicated in degrees centigrade and the abbreviations have the meaning common in the art.

EXAMPLE 1

Preparation of 2-methylene-6,6-dimethyl-1-but-3-en-1-yl-cyclohexane

A solution of butyl-lithium in hexane (520 ml; 1.45N) was added under nitrogen within 10 mn at a temperature of about 15°–17° to a solution of methyl betacyclogeranate (100 g; 0.549M) in 1500 ml of anhydrous tetrahydrofuran (THF) in a 4 l reaction flask equipped with mechanical stirrer. The reaction mixture was left to react for 5 mn at 15°, then 320 ml of a 2.40N solution of allyl-magnesium chloride in THF (1.4 equiv.) were added thereto. The temperature raised slowly and at 26° the mixture was cooled with an external ice bath so that the temperature did not raise beyond 30°–35°. After 10 mn, the mixture was hydrolyzed by pouring it onto a mixture of ice and an aqueous solution of ammonium chloride whereupon, after separation of the two layers formed and washing of the organic phase with a saturated aqueous solution of sodium chloride, the solvent was stripped off. By simple distillation, two fractions of a raw material were obtained having b.p. 65°/6.65 Pa (purity: 92%; 83.20 g) and b.p. 65°–75°/6.65Pa (purity: 60%; 9.05 g). Yield: 80%.

A further purification gave a product having b.p. 87°/2.66×10² Pa. The product thus obtained was converted into gamma-damascone by isomerization by means of an acid treatment with p-toluenesulfonic acid.

By carrying out the reaction under conditions identical to those described in the above example on methyl beta-safranate (20 g) instead of methyl beta-cyclogeranate, 19.1 g of 2-methylene-6,6-dimethyl-1-but-3-en-1-oylcyclohex-3-ene were obtained.

Methyl beta-safranate used as starting material in the above described process was prepared as indicated in European Patent No. 46606.

EXAMPLE 2

Preparation of 2-methylene-6,6-dimethyl-1-pentan-1-oyl-cyclohexane

A solution of 14.3 ml (0.020M) of butyl-lithium in hexane was added at −78° to a solution of 2.6 g of S-phenyl 2,6,6-trimethyl-1-cyclohexene-1-carbothioate (0.010M). The temperature raised to room temperature, then, after about 30 mn, the hydrolysis was carried out by means of a saturated aqueous solution of ammonium chloride as indicated in the previous example. The organic phase was separated, washed until neutrality and dried. After solvent evaporation, a distillation gave 1.25 g of the desired ketone having b.p. 100°–150°/6.6 Pa. The starting thioester can be prepared from 2,6,6-trimethyl-cyclohex-1-enoyl chloride according to the following method.

In a three-necked reaction flask, 6.46 g (0.051M) of oxalyl chloride were added dropwise a solution of beta-cyclogeranic acid (5.73 g; 0.034M) in 60 ml of methylene chloride. The reaction mixture was then heated to reflux until gas evolution ceased. The volatiles were stripped off in vacuum.

In a separate reaction flask, 3.57 g of a solution of thiophenol (0.032M) in 40 ml of THF were treated with 22.5 ml of butyl-lithium (0.032M). To the resulting solution, there was added a solution of the acyl chloride separately prepared as indicated above in THF while the temperature was kept at 10°. After one night at room temperature, the reaction mixture was poured onto a mixture consisting of ice and a 5% aqueous solution of NaOH. The mixture was extracted with ether, and the organic extracts were washed. Then, after the usual treatments of drying and separation, a distillation gave 6.5 g of the desired S-phenyl carbothioate.

NMR (CDCl₃; 60 MHz): 1.15 (6H, s); 1.55 (4H, m); 1.85 (3H, s); 1.7–2.1 (2H, m); 7.35 (5H, s) delta ppm.

By operating in the same way and starting from S-phenyl 2,6,6-trimethylcyclohex-2-en-1-carbothioate, there was obtained 2,6,6-trimethyl-1-pentanoylcyclohex-2-ene.

What we claim is:

1. A process for the preparation of cycloaliphatic ketones having the formula

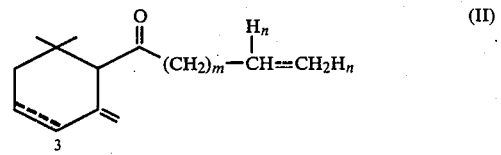

wherein index m designates an integer 0, 1 or 2, n stands for 0 or 1 and the dotted lines represent an optional supplemental bond, which comprises effecting the following subsequent reaction steps:

a. deprotonation of an ester having the formula

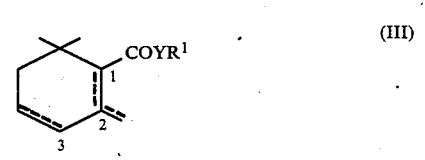

having either an isolated double bond in position 1 or 2 (exocyclic), or two conjugated double bonds in position 1 and 3 or 2 (exocyclic) and 3 as indicated by the dotted lines, and wherein symbol R′ represents a linear or branched alkyl radical, preferably a $C_1$–$C_6$ alkyl radical, or a substituted or unsubstituted phenyl, and wherein Y designates an oxygen or a sulphur atom by reacting said ester with a strong base;

b. adding to the thus formed enolate having the formula

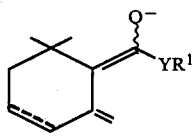 (IV)

an organo-metallic compound having the formula

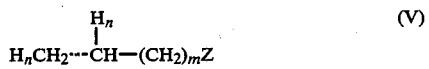 (V)

wherein m stands for an integer 0, 1 or 2, n has a value of 0 or 1, Z represents a MgX radical or an alkali metal, with X designating a halogen atom, and the dotted lines represent an optional supplemental bond; and c. hydrolyzing the resulting product.

2. Process according to claim 1 wherein the strong base is an alkali metal alkyl derivative or an alkali metal amide.

3. Process according to claim 2 wherein the strong base is chosen among the group of propyl-lithium, butyl-lithium, or lithium dimethyl-, lithium diethyl- and lithium diisopropyl-amide.

4. The process according to claim 1, 2 or 3 wherein the base is used in an amount higher than the equivalent amount of starting ester III.

5. Process according to claim 1 wherein the organo-metallic compound of formula (V) is allyl-magnesium chloride.

6. Process according to claim 5 wherein allyl-magnesium chloride is used in an amount higher than the equivalent amount of starting ester (III).

7. Process according to claim 1 wherein the starting ester (III) is methyl beta- or gamma-cyclogeranate, the strong base is butyl-lithium and the organo-metallic compound is allyl-magnesium chloride, and the obtained product after hydrolysis is 2-methylene-6,6-dimethyl-1-but-3-en-1-oyl-cyclohexane.

8. Process according to claim 1 wherein the starting ester (III) is methyl beta-safranate, the strong base is butyl-lithium and the organo-metallic compound is allyl-magnesium chloride, and the obtained product after hydrolysis is 2-methylene-6,6-dimethyl-1-but-3-en-1-oyl-cyclohex-3-ene.

* * * * *